(12) United States Patent
Sutton

(10) Patent No.: US 12,121,076 B2
(45) Date of Patent: Oct. 22, 2024

(54) THERAPEUTIC BRASSIERE GARMENT

(71) Applicant: Troy Sutton, New York, NY (US)

(72) Inventor: Troy Sutton, New York, NY (US)

( * ) Notice: Subject to any disclaimer, the term of this patent is extended or adjusted under 35 U.S.C. 154(b) by 217 days.

(21) Appl. No.: 17/555,578

(22) Filed: Dec. 20, 2021

(65) Prior Publication Data
US 2023/0009346 A1 Jan. 12, 2023

Related U.S. Application Data

(60) Provisional application No. 63/220,750, filed on Jul. 12, 2021.

(51) Int. Cl.
*A41C 3/00* (2006.01)
*A41C 3/12* (2006.01)
*A61F 7/02* (2006.01)

(52) U.S. Cl.
CPC .............. *A41C 3/0064* (2013.01); *A41C 3/12* (2013.01); *A61F 7/02* (2013.01); *A61F 2007/0234* (2013.01); *A61F 2007/0242* (2013.01)

(58) Field of Classification Search
CPC ....... A41C 3/14; A41C 3/0064; A41C 3/0035; A41C 3/142
USPC ............................................................ 450/1
See application file for complete search history.

(56) References Cited

U.S. PATENT DOCUMENTS

| | | | | |
|---|---|---|---|---|
| 1,391,936 | A * | 9/1921 | Bosky | A41C 3/00 450/1 |
| 6,394,879 | B1 * | 5/2002 | Paige | A41C 3/04 450/38 |
| 6,464,717 | B1 * | 10/2002 | Smith | A61F 7/02 450/58 |
| 8,597,072 | B1 * | 12/2013 | Lucas | A41C 3/0035 2/247 |
| 8,926,398 | B1 * | 1/2015 | Mendeleev | A41C 3/08 450/61 |
| 9,781,954 | B1 * | 10/2017 | Osetek | A41C 3/0057 |
| 2006/0154566 | A1 * | 7/2006 | Nunez | A41C 3/0064 450/37 |
| 2013/0232661 | A1 * | 9/2013 | Huntley | A41D 1/215 2/104 |
| 2014/0329438 | A1 * | 11/2014 | Horii | A41C 3/142 450/41 |
| 2016/0165962 | A1 * | 6/2016 | Hayes | A41C 3/0064 450/55 |
| 2018/0295893 | A1 * | 10/2018 | Corley | A41C 3/146 |

(Continued)

*Primary Examiner* — Timothy K Trieu
(74) *Attorney, Agent, or Firm* — Brennan, Manna & Diamond, LLC

(57) ABSTRACT

The present invention relates to a therapeutic brassiere garment for healing or easing breast pain related to breast-feeding, surgery, menstruation, childbirth and more. The therapeutic brassiere garment features front panels with cups for covering and supporting breasts. Each front panel includes a pocket for holding a therapeutic pad. The therapeutic pad can be put in a microwave for heating and/or in a refrigerator/freezer for cooling and can then be accommodated in the pockets of the garment for providing hot and/or cold therapy. The garment comes in different sizes and styles available for pain relief due to any type of condition. Each pocket includes three sewn sides and an opening for preventing the therapeutic pad from slipping into inappropriate or uncomfortable positions while wearing the brassiere garment.

13 Claims, 6 Drawing Sheets

(56) References Cited

U.S. PATENT DOCUMENTS

| | | | | |
|---|---|---|---|---|
| 2018/0317571 A1* | 11/2018 | Caden | ................. | A41C 3/0057 |
| 2021/0361473 A1* | 11/2021 | Crowe | ................ | H01M 10/425 |
| 2023/0091122 A1* | 3/2023 | Harrison | .............. | A41D 27/133 |
| | | | | 450/57 |

* cited by examiner

THERAPEUTIC BRASSIERE GARMENT

CROSS-REFERENCE TO RELATED APPLICATION

The present application claims priority to, and the benefit of, U.S. Provisional Application No. 63/220,750, which was filed on Jul. 12, 2021 and is incorporated herein by reference in its entirety.

FIELD OF THE INVENTION

The present invention relates generally to the field of brassiere garments. More specifically, the present invention relates to a therapeutic brassiere garment for healing or easing breast pain related to breastfeeding, surgery, menstruation, childbirth and more. More specifically, the therapeutic brassiere garment includes a pair of front panels with cups, with each front panel including a pocket for holding a therapeutic pad. The therapeutic pad can be put in a microwave for heating, or in a refrigerator/freezer for cooling, and then can be placed in the pockets of the garment for providing hot and cold therapy. The garment comes in different sizes, shapes and styles available for pain relief due to any type of physical condition. The therapeutic pads are discreetly placed within the pockets without taking up the entire space within the bra pocket. The pockets can be sewn to the interior surface of the front panels or cups. Accordingly, the present disclosure makes specific reference thereto. Nonetheless, it is to be appreciated that aspects of the present invention are also equally applicable to other like applications, devices, and methods of manufacture.

BACKGROUND

By way of background, pain in the breasts is one of the worst experiences for a woman. The pain in breasts can be caused due to a variety of reasons that vary from woman to woman. For breastfeeding women, a clogged or plugged milk duct, mastitis (a breast infection that can develop while breastfeeding) and fibrocystic breast tissue are some of the reasons for unbearable and uncomfortable breast pain. The aforementioned conditions make women reluctant to breastfeed due to the pain.

Some women experience breast pain due to taking certain medications, such as digitalis, methyldopa, spironolactone, diuretics, chlorpromazine or oxymetholone, a breast injury or even water retention. This pain makes women reluctant to take such medicines.

Breast surgeries such as an open excisional biopsy (lumpectomy) or needle aspiration for obtaining a sample of a suspected tumor for analysis, Mastopexy (breast lift), breast augmentation for cosmetic reasons and Mammoplasty (breast reduction) for cosmetic reasons, cause an incision or a penetration of the skin overlying the breast. After such surgeries, women can face unbearable pain, and end up taking pain killers, which are not safe for their long-term health.

Currently available post-surgery brassiere garments and therapeutic garments worn by patients provide support for the breasts, but do not provide a convenient way of performing hot and cold therapy of breast tissues. Using hot and cold therapy has been a long-time remedy doctors have recommended. Heretofore known therapeutic brassiere garments do not provide such cost-effective, continuous, comfortable, discreet, and efficient hot and cold therapy.

Therefore, there exists a long felt need in the art for an improved therapeutic brassiere garment that provides relief from breast pain due to any type of condition. There is also a long felt need in the art for an improved therapeutic brassiere garment that can provide hot and cold therapy to the breasts of the wearer. Additionally, there is a long felt need in the art for an improved therapeutic brassiere garment that can be worn like a conventional bra underneath any garment. Moreover, there is a long felt need in the art for an improved therapeutic brassiere garment that comes in a variety of sizes and shapes to fit all women. Furthermore, there is a long felt need in the art for an improved therapeutic brassiere garment that eliminates use of additional post-surgery garments as the healing process progresses. Finally, there is a long felt need in the art for an improved therapeutic brassiere garment that heals breast pain related to breastfeeding, surgery, menstruation, childbirth and other reasons, by providing hot and cold therapy to the breast tissue.

The subject matter disclosed and claimed herein, in one embodiment thereof, comprises a pain-healing brassiere garment that is designed to heal breast pain related to breastfeeding, surgery, menstruation, childbirth and more. The brassiere garment comprises: two front panels including cups for covering the breasts of a wearer; each front panel including an exterior surface and an interior surface; the exterior surface is exposed outwardly and the interior surface is overlaid on the wearer's skin; the interior surface of each front panel including a sewn pocket wherein each pocket includes a top or side opening; and a pair of therapeutic pads wherein one therapeutic pad is inserted and removed therefrom each pocket, such that the cooling or heating effect of each therapeutic pad affects the breast tissues for healing when the brassiere garment is worn by a wearer. The brassiere garment further includes a pair of shoulder straps operable to secure the brassiere garment over the shoulders of the wearer and an elastic waistline for preventing the brassiere slipping off the torso of the wearer.

In this manner, the improved therapeutic brassiere garment of the present invention accomplishes all of the forgoing objectives and provides a relatively safe, comfortable, discreet, convenient and cost-effective breast pain healing device, thereby enabling users to heat or cool the therapeutic pads prior to inserting them into the pockets for customizing the pain relief effect on the breasts. The bra helps alleviate any breast pain associated with numerous conditions like breastfeeding, surgery, menstruation, childbirth or any other medical condition.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a pain-healing brassiere garment. The brassiere garment is designed for providing healing or easing breast pain related to breastfeeding, surgery, menstruation, childbirth and more. The brassiere garment further comprising: two front panels including cups for covering the breasts of a wearer; each front panel including an exterior surface and an interior surface; the exterior surface is exposed outwardly and the interior surface is overlaid on the wearer's skin; the interior surface of each front panel including a sewn pocket wherein each pocket includes a top opening; and a pair of therapeutic pads wherein one therapeutic pad can be inserted and removed therefrom each pocket, such that the cooling or heating effect of each therapeutic pad affects the breast tissues for healing when the brassiere garment is worn by a wearer. The brassiere garment further includes a pair of shoulder straps operable to secure the brassiere garment over the shoulders of the wearer and an elastic waistline for preventing the brassiere from slipping off the torso of the wearer.

In yet another embodiment, each pocket can cover a minority portion of the breast in the range of from about 30% to about 50%, and can be positioned to cover the nipples of the wearer. Alternatively, each pocket can cover a majority portion of the breast in the range of from about 50% to about 80%, and can be positioned to cover the nipples of the wearer.

In yet another embodiment of the present invention, a therapeutic brassiere garment for a wearer is disclosed. The therapeutic brassiere garment includes two cups for covering the breasts of a wearer, a pocket sewn to an interior surface of each cup, wherein each pocket is configured to receive and accommodate a therapeutic pad for providing either hot therapy or cold therapy to the breast tissues of the wearer, and the pocket acts as a barrier between the skin of the wearer and the therapeutic pad, thereby enabling a comfortable level of heat and cold of the pad to be transferred to the skin of the wearer. Each pocket includes three sewn ends and a top opening for preventing the therapeutic pad from slipping or sliding into inappropriate or uncomfortable positions while wearing the brassiere garment.

In yet another embodiment of the present invention, the therapeutic pad can include a thermal-conducting material such as iron or charcoal. Alternatively, the pad can include thermally-conducting gel and/or gel beads in standard packs covered in a soft material.

In yet another embodiment of the present invention, the therapeutic pads can be kept and/or cooled in a refrigerator or freezer in order to provide cold therapy. Further, the therapeutic pads can be safely heated in a microwave for absorbing heat in order to provide hot therapy.

In yet another embodiment of the present invention, a healing bra is disclosed. The healing bra is designed for healing pain and sore tissues of the breasts of a wearer by providing hot and cold therapy. The healing bra includes a pair of pockets sewn on an interior surface of each panel or cup in the front portion of the bra for covering the breasts of the wearer, each pocket of the pair of pockets receives and stores a therapeutic pad for holding the therapeutic pad over a portion of the breast, and provides either hot or cold therapy. The pads are discreetly placed within the pockets without taking up or consuming the entire space within the bra pocket.

In yet another embodiment, the pockets are water-absorbing and thermally-conducting, enabling efficient hot and cold therapy without causing any irritation to the skin of the wearer.

In yet another embodiment of the present invention, each therapeutic pad provides hot or cold therapy to at least 50% of the breast portion. Alternatively, each therapeutic pad provides hot or cold therapy to at least 80% of the breast portion. In one potential embodiment, each therapeutic pad provides hot or cold therapy to at least 20% of the breast portion adjacent to and circumscribing the nipple.

In yet another embodiment, the healing bra is used as a post-surgical bra to help with pain in the breasts caused by using therapy medications, taking certain medications, such as methyldopa, spironolactone, chlorpromazine or oxymetholone, a breast injury or water retention. Further, the healing bra helps in curing and healing Mastitis.

In yet another embodiment of the present invention, a method of healing pain in the breast tissues is described. The method includes wearing a therapeutic bra, wherein the bra includes a pair of shoulder straps operable to secure the bra over shoulders, an elastic waistline for stabilizing the bra around the torso, a pair of cups or panels for covering the breasts, and a pocket disposed on an interior surface of each cup or panel. The method further includes the steps of heating or cooling one or a pair of therapeutic pads by heating or cooling the pads in a microwave or a freezer, respectively, and placing the therapeutic pads in the pockets for providing hot or cold therapy to the wearer of the therapeutic bra.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
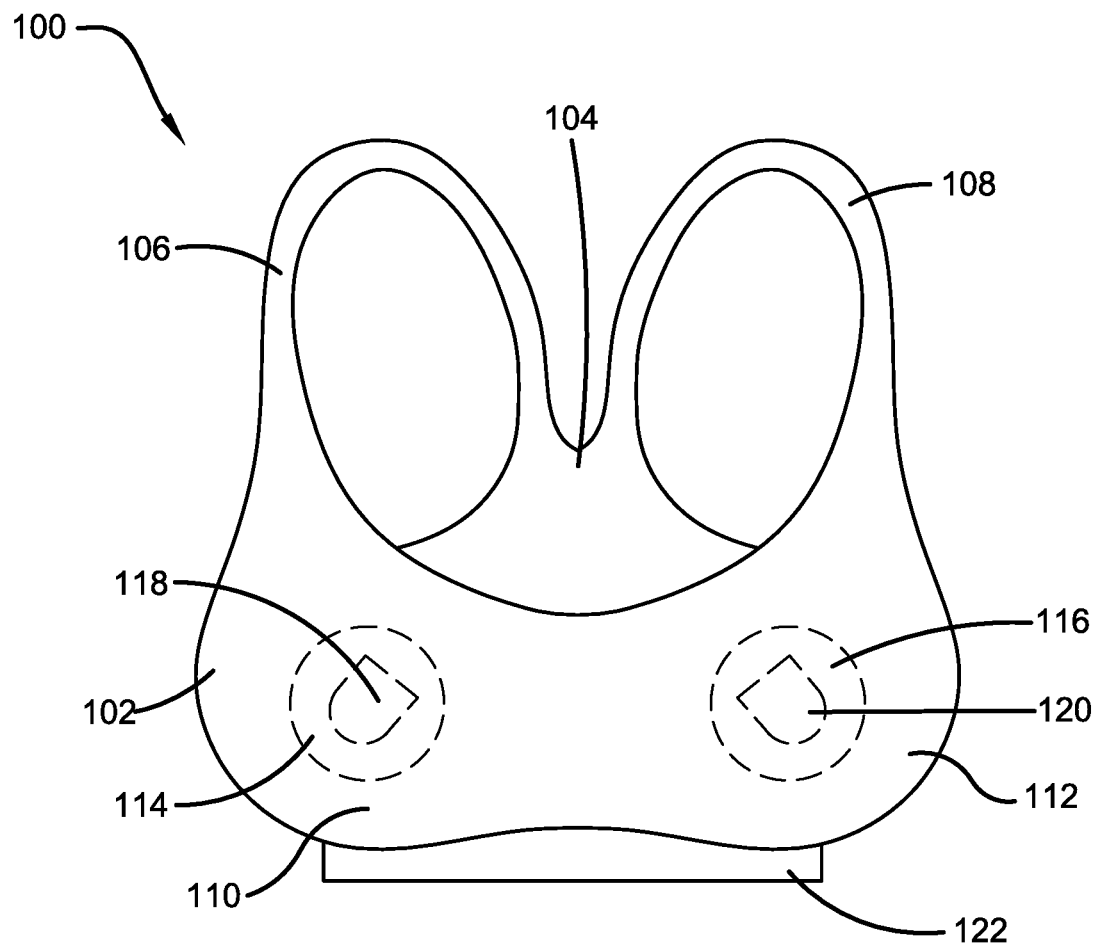
FIG. 1 illustrates a front perspective view of one potential embodiment of a healing brassiere garment of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long felt need in the art for an improved therapeutic brassiere garment that provides relief from breast pain due to any type of condition. There is also a long felt need in the art for an improved therapeutic brassiere garment that can provide hot and cold therapy to the breasts of the wearer. Additionally, there is a long felt need in the art for an improved therapeutic brassiere garment that can be worn like a conventional bra underneath any garment. Moreover, there is a long felt need in the art for an improved therapeutic brassiere garment that comes in a variety of sizes and shapes to fit all women. Furthermore, there is a long felt need in the art for an improved therapeutic brassiere garment that eliminates the use of additional post-surgery garments as the healing process progresses. Finally, there is a long felt need in the art for an improved therapeutic brassiere garment that heals breast pain related to breastfeeding, surgery, menstruation, childbirth and other reasons, by providing hot and cold therapy to the breast tissue.

The present invention, in one potential embodiment, includes a novel therapeutic brassiere garment for a wearer. The therapeutic brassiere garment features two cups for covering the breasts of a wearer, a pocket sewn to an interior surface of each cup wherein each pocket is configured to receive and accommodate a therapeutic pad for providing either hot therapy or cold therapy to the breast tissue of the wearer. The pocket acts as a barrier between the skin of the wearer and the therapeutic pad, thereby enabling a comfortable level of heat or cold of the pad to be transferred to the skin of the wearer.

Referring initially to the drawings, FIG. 1 illustrates a front perspective view of one potential embodiment of the healing brassiere garment of the present invention in accordance with the disclosed architecture. The healing bra 100 of the present invention includes an enhanced bra that heals breast pain related to breastfeeding, surgery, menstruation, childbirth and other conditions. More specifically, the healing bra 100 includes an exterior layer 102 and an interior layer 104. Preferably, the exterior layer 102 and the interior layer 104 can be integrally and seamlessly connected to each other to form a unitary and single piece brassiere garment 100. The healing bra 100 includes a first (right) shoulder strap 106, a second (left) shoulder strap 108 and a head opening, thereby enabling a user to easily wear the bra 100 for use. The bra 100 includes a first panel 110 and a second panel 112 countered like the natural breasts of a user. Both the first (right) panel 110 and the second (left) panel 112 are designed to fit over the breasts and to support the breasts from underneath and from the sides. The first panel 110 can optionally have a first molded contoured cup 114 and the second panel 112 can optionally have a second molded contoured cup 116, for providing additional support to the breasts and also for providing shape to the breasts when the bra 100 is worn by the user.

The molded contoured cups 114, 116 generally have a hemispherical shape that can overlay the breast of a subject. However, the cups 114, 116 may vary in diameter, depth, concavity and more. Further, the first molded cup 114 and the second molded cup 116 can include the same or different dimensions.

Figure 2:
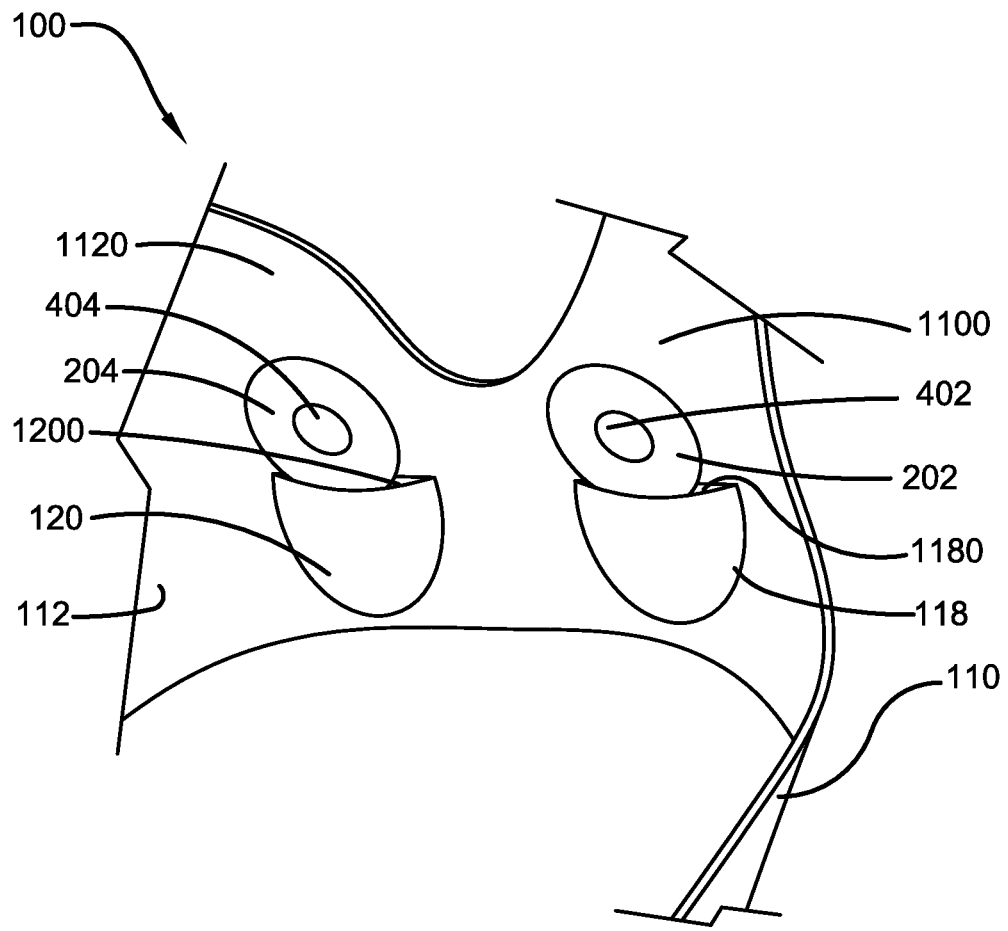
FIG. 2 illustrates a rear internal view of one potential embodiment of the healing brassiere garment of the present invention showing how the therapeutic pads are stored in the pockets for healing or easing breast pain in accordance with the disclosed architecture.

For healing breasts and providing comfort to the user in pain after breastfeeding, recovery from surgery and more, the interior layer of the first panel 110 includes a first pocket 118 and the second panel 112 includes a second pocket 120. The pockets 118, 120 can be sewn into the interior layers of the respective panels and are designed for storing therapeutic pads as best shown in FIG. 2. The pockets 118, 120 can be discretely disposed and sewn to the first panel 110 and the second panel 112, respectively, without taking up the entire space of the respective cups 114, 116.

The healing bra 100 includes an elastic waistline 122 that prevents slippage of the bra 100 when worn by a user. The bra 100 can include an underwire assembly or can come in a variant without an underwire assembly. The healing brassiere garment 100 can include a material consisting of one or more of tricot, microfiber, raschel, spandex, silk, silk combined with spandex, nylon, polyester, cotton and more. It should be understood that the bra 100 conforms to the natural breasts' contour without exerting substantial pressure thereto.

FIG. 2 illustrates a rear internal view of the healing brassiere garment 100 of the present invention, showing how the therapeutic pads are stored in the pockets for healing or easing breast pain in accordance with the disclosed architecture. The first pocket 118 can be sewn on the interior surface 1100 of the first panel 110 and is configured to store a first therapeutic pad 202. Similarly, the second pocket 120 can be sewn on the interior surface 1120 of the second panel 112 and is configured to store a second therapeutic pad 204. The first pocket 118 includes an opening 1180 through which the first therapeutic pad 202 can be inserted and removed therefrom and similarly, the second pocket 120 includes an opening 1200 through which the second therapeutic pad 204 can be inserted and removed therefrom. The contoured cups can be detachably-attached or integrated to the panels 110,112. The pockets 118, 120 can be sewn to the respective contoured cups 114, 116.

The pockets 118, 120 in accordance with the present invention, can be sewn to the interior surface of each cup/panel for safe, discreet and comfortable support of the therapeutic pads 202, 204 used for the therapeutic properties described supra. The dimensions of the pockets 118, 120 are such that they ensure that where necessary, the therapeutic pads 202, 204 do not slip or slide into inappropriate or uncomfortable positions. The therapeutic pads can be of a variety of different shapes and dimensions, and the pockets 118, 120 are operable to retain pads of different shapes and dimensions. Accordingly, the present invention provides pockets 118, 120 of such a construction that the therapeutic pads 202, 204 can be inserted and removed therefrom. In use, the pockets enable the brassiere garment 100 to be worn without fear of the pads 202, 204 being dislodged, falling away, or slipping out. The pockets 118, 120 can include a material that is extremely soft to the skin of the wearer and enables the hot or cold temperature to be transferred to the breast tissue. The pockets 118, 120 are not visible from an outside or exterior view, thereby making the wearer comfortable in wearing the healing bra 100 of the present invention.

The therapeutic pads 202, 204 are commercially available with the healing bra 100 of the present invention and improve healing of the breasts of the wearer. The therapeutic pads 202, 204, when stored in the pockets 118, 120 and worn by the wearer, help in eliminating a medical condition and also reduce severity and pain associated therewith. The medical condition may include, for example, tissue damage, irritation, breast pain related to breastfeeding, surgery, menstruation, childbirth, pain at the area of incisions, redness, swollen tissue and many more. Further, the therapeutic pads 202, 204, when worn inside the bra 100 provide hot and/or cold breast therapy that relieves the pain and aches caused by inflammation, swelling and enlarged ducts.

Preferably, the therapeutic pads 202, 204 can act as heating pads or cooling pads based on the requirements of the users. The therapeutic pads 202, 204 can be heated by putting them in a microwave to increase the temperature of the pad in order to apply deep heat to the breast tissue for an extended period of time (i.e. up to 1 hour). Alternatively, the therapeutic pads can be chilled by putting them in a refrigerator or freezer to decrease the temperature of the pad in order to apply deep cooling to the breast tissue for an extended period of time (i.e. up to 1 hour). The therapeutic pads 202, 204 preferably have natural heating ingredients such as iron or charcoal, that are both safe for the user and effective in absorbing and retaining heat. Alternatively, the therapeutics pads 202, 204 can include gel beads covered in a soft material.

The therapeutic pads 202, 204, when used for cold therapy, reduce blood flow and help in reducing inflammation and swelling of the tissue adjacent to the pads. The heat therapy improves blood flow and increases muscle flexibility. The therapeutics pads 202, 204 are reusable, and are designed to conform to the curve of the breasts of the wearer. The heat or cold of the therapeutic pads is evenly absorbed and can be evenly dissipated or distributed to the coverage area over the associated tissue area. The therapeutic pads and pockets can act as medical-grade hot and cold packs for the wearer.

Figure 3:
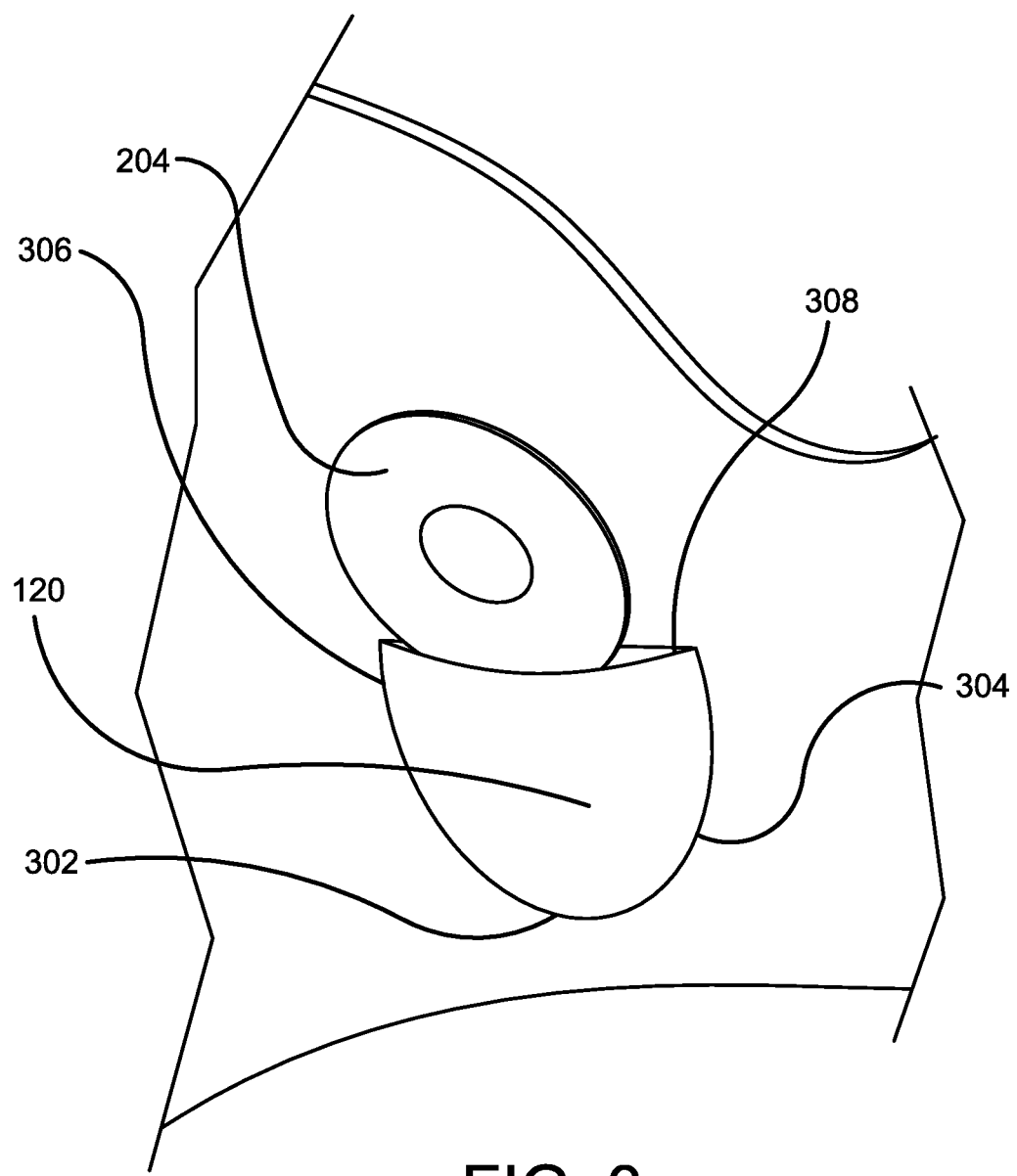
FIG. 3 illustrates an enlarged view of one potential embodiment of the pocket sewn to the interior surface of the front panel or cup of healing brassiere garment of the present invention for accommodating a therapeutic pad in accordance with the disclosed architecture.

FIG. 3 illustrates an enlarged view of the pocket sewn to the interior surface of the front panel or cup of a healing brassiere garment 100 of the present invention for accommodating a therapeutic pad in accordance with the disclosed architecture. Each pocket sewn on the interior surface of the front panel is designed to receive and accommodate a therapeutic pad. As an example, the second (left) pocket 120 can be sewn along three sides or edges 302, 304, 306 and can include a top opening 308. The therapeutic pad 204 can be placed in the pocket 120 through the opening 308 and can be accommodated in the cavity formed by the sewn edges 302, 304, 306. Each pocket can cover a minority portion or area of the breast in the range of from about 30% to about 50%, and can be positioned to cover the nipples of the wearer. Alternatively, each pocket can cover a majority portion or area of the breast in the range of from about 50% to about 80%, and can be positioned to cover the nipples of the wearer. The pockets can be designed in a shape conforming and aligning to the breast shape and size for enabling effective therapy to the breast.

Figure 4:
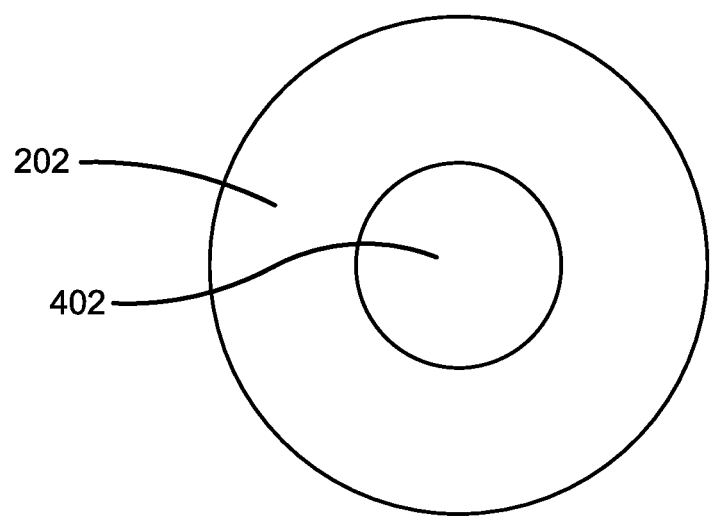
FIG. 4 illustrates a perspective view of one potential embodiment of the therapeutic pad used for providing cold and hot therapy by accommodating in the healing bra of the present invention in accordance with the disclosed architecture.

FIG. 4 illustrates a perspective view of the therapeutic pad used for providing cold and hot therapy by positioning in the healing bra 100 of the present invention in accordance with the disclosed architecture. For example, the therapeutic pad 202 is flexible and can include a circular shape with a diameter in the range from about 1 inch to about 8 inches, for providing appropriate coverage of the breast as per the requirements of the users. In the present embodiment, the pads 202, 204 can include a circular hole 402, 404, respectively, for circumscribing the nipple when the healing bra is worn by a wearer. The therapeutic pads 202, 204 can include natural heating ingredients or elements such as iron or charcoal, that are safe for the user and comprise increased temperature sensitivity and effectiveness. Alternatively, the therapeutic pads can include gel beads covered in a soft material which is machine-washable.

The therapeutic pad can include a layer of antimicrobial coating that eliminates microbes. The therapeutic pad can be thin and flexible and constructed to prohibit any irritation to the wearer.

Figure 5:
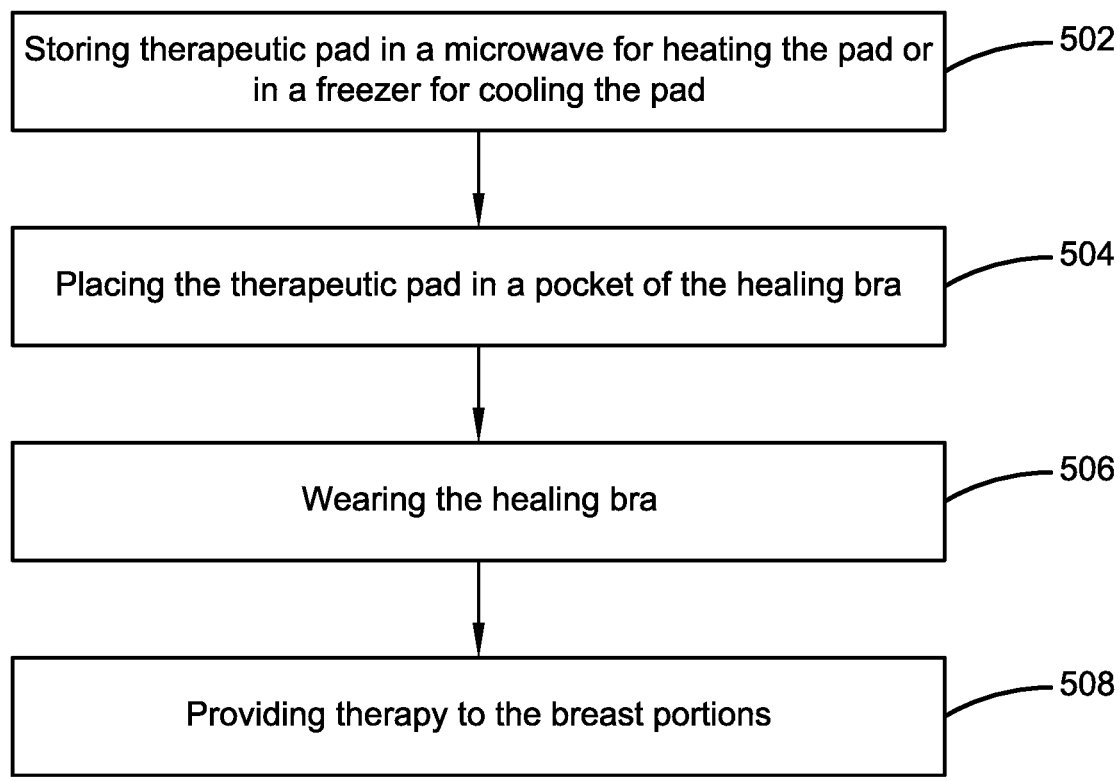
FIG. 5 illustrates a flow diagram showing exemplary steps in providing therapy by wearing one potential embodiment of the healing bra of the present invention in accordance with the disclosed architecture.

FIG. 5 illustrates a flow diagram showing exemplary steps in providing therapy by wearing the healing bra of the present invention in accordance with the disclosed architecture. Initially, based on the requirement of a user incorporating a hot therapy or a cold therapy, one or more therapeutic pads can be heated in a microwave for heating the pad, or stored in a freezer for cooling the pad (Block 502). Then, the hot or cold therapeutic pad is placed in a pocket of the healing bra (Block 504). Next, the healing bra with accompanied therapeutic pads is worn by a wearer (Block 506) and the therapeutic pads start providing the hot or cold therapy to the wearer for healing pain and inflammation in the breast tissue (Block 508).

Figure 6:
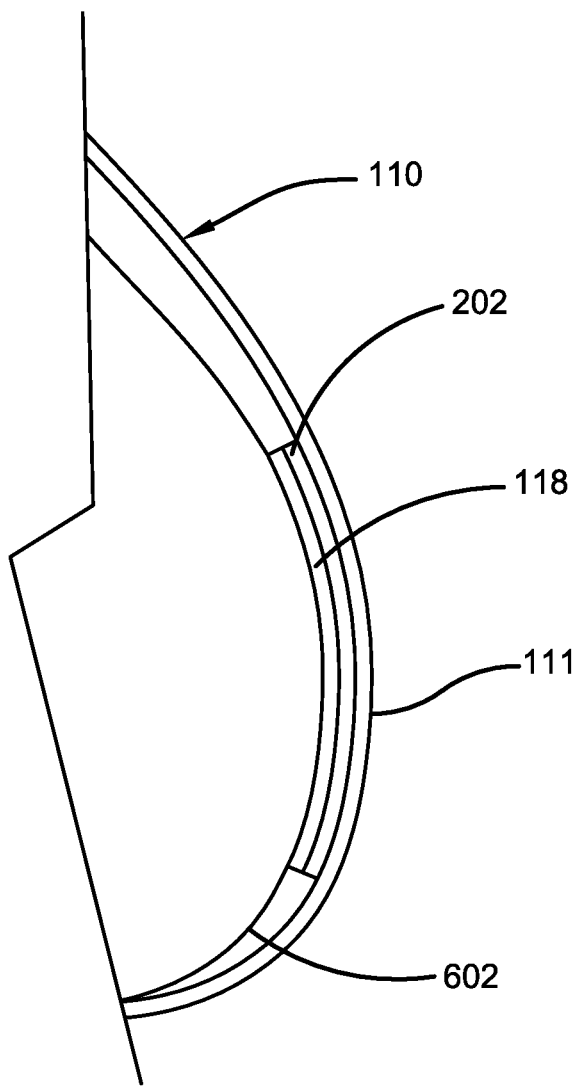
FIG. 6 illustrates a sectional view showing the contact of one potential embodiment of the pocket and the therapeutic pad of the healing bra of the present invention with the breast of a wearer in accordance with the disclosed architecture.

FIG. 6 illustrates a sectional view showing the contact of the pocket and the therapeutic pad of the healing bra of the present invention with a breast of a wearer in accordance with the disclosed architecture. As shown in the FIG. 6, the breast 602 of a wearer touches the sleeve of the pocket 118 that accommodates or holds the therapeutic pad 202. The heating or cooling effect of the pad 202 can reach or transfer to the breast 602 of the wearer through the thermally-conducting pocket 118. The pad 202 also contacts the interior layer of the front panel 110 and is not visually exposed to the front side 111 of the front panel 110.

The therapeutic pads can be comfortably and discreetly placed within the pockets without taking up the entire space within the bra pocket, thus allowing the bra to be work in public, to work, or wherever the wearer prefers.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "therapeutic bra", "healing bra", "device", "healing brassiere garment", and "therapeutic brassiere garment" are interchangeable and refer to the therapeutic brassiere garment 100 of the present invention.

Notwithstanding the forgoing, the therapeutic brassiere garment 100 of the present invention can be of any suitable size and configuration as is known in the art without affecting the overall concept of the invention, provided that it accomplishes the above-stated objectives. One of ordinary skill in the art will appreciate that the size, configuration, and material of the therapeutic brassiere garment 100 as shown in the FIGS. are for illustrative purposes only, and that many other sizes and shapes of the therapeutic brassiere garment 100 are well within the scope of the present disclosure. Although the dimensions of the therapeutic brassiere garment 100 are important design parameters for user convenience, the therapeutic brassiere garment 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments including different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A therapeutic healing brassiere comprising: a first shoulder strap and a second shoulder strap; a first panel and a second panel configured to fit over breasts of a user to support the breasts from underneath; a first pocket comprising a top opening and attached on three sides to an interior surface of the first panel; a second pocket comprising a top opening and attached on three sides to an interior surface of the second panel; a first molded contoured cup integrated into the first panel; a second molded contoured cup integrated into the second panel; said first pocket configured to secure a first therapeutic pad and said second pocket configured to secure a second therapeutic pad; said first pad selectively removable from said first pocket and said second pad selectively removable from said second pocket; and
    wherein the therapeutic healing brassiere is a tricot therapeutic healing brassiere; and
    wherein the first and second therapeutic pads each comprise an iron heating element and an antimicrobial layer;
    further comprising an elastic waistline for prohibiting slippage of said therapeutic healing brassiere when worn by the user; wherein said first pad comprises a first circular hole for circumscribing a first nipple of the user and said second pad includes a second circular hole for circumscribing a second nipple of the use.

2. The therapeutic healing brassiere of claim 1, wherein said first pad and said second pad are freezable for selective cooling.

3. The therapeutic healing brassiere of claim 2, wherein said first pad and said second pad are reusable.

4. The therapeutic healing brassiere of claim 2, wherein said first pad and said second pad include a circular shape with a diameter in the range from about 1 inch to about 8 inches.

5. The therapeutic healing brassiere of claim 1 wherein said first contoured cup includes a first dimension and said second contoured cup includes a second dimension, said first dimension is different from said second dimension.

6. A therapeutic healing brassiere comprising:
    a first shoulder strap and a second shoulder strap;
    a first panel and a second panel configured to fit over breasts of a user to support the breasts from underneath;
    a first pocket comprising a top opening and attached on three sides to an interior surface of the first panel;
    a second pocket comprising a top opening and attached on three sides to an interior surface of the second panel;
    a first molded contoured cup attached to the first panel;
    a second molded contoured cup attached to the second panel;
    said first pocket configured to secure a first therapeutic pad and said second pocket configured to secure a second therapeutic pad;
    said first pad selectively removable from said first pocket and said second pad selectively removable from said second pocket;
    said first pad and said second pad are microwavable for selective heating;
    said first pad and said second pad are coolable for selective cooling; and
    said first pad includes a first circular hole for circumscribing a first nipple of the user and said second pad includes a second circular hole for circumscribing a second nipple of the user; and
    wherein the therapeutic healing brassiere is a silk therapeutic healing brassiere; and
    wherein the first and second therapeutic pads each comprise a charcoal heating element and an antimicrobial layer; and
    wherein the first and second molded contoured cups are removably attached to the respective first and second panels.

7. The therapeutic healing brassiere of claim 6, wherein said first pad and said second pad are reusable.

8. The therapeutic healing brassiere of claim 7, wherein said first pad and said second pad include a circular shape with a diameter in the range from about 1 inch to about 8 inches.

9. A therapeutic healing brassiere comprising: a first shoulder strap and a second shoulder strap; a first panel and a second panel configured to fit over breasts of a user to support the breasts from underneath and from the sides; a first pocket comprising a top opening and sewn around a perimeter to an interior surface of the first panel; a second pocket comprising a top opening and sewn around a perimeter to an interior surface of the second panel; a first molded contoured cup integrated into the first panel; a second molded contoured cup integrated into the second panel; said first pocket configured to secure a first therapeutic pad and said second pocket configured to secure a second therapeutic pad; said first pad selectively removable from said first pocket and said second pad selectively removable from said second pocket; said first pad and said second pad are microwavable for selective heating; said first pad and said second pad are coolable freezable for selective cooling; and said first pad and said second pad are reusable; and wherein the therapeutic healing brassiere is a raschel therapeutic healing brassiere; and wherein the first and second therapeutic pads each comprise an iron or a charcoal heating element and an antimicrobial coating;
    and wherein the first and second molded contoured cups are removably attached to the respective first and second panels; wherein said first pad includes a first circular hole for circumscribing a first nipple of the user and said second pad includes a second circular hole for circumscribing a second nipple of the user.

10. The therapeutic healing brassiere of claim 9, wherein each said first pocket and said second pocket cover a minority area of the respective breast in the range of from about 30% to about 50%.

11. The therapeutic healing brassiere of claim 10, wherein said first pad and said second pad include a circular shape with a diameter in the range from about 1 inch to about 8 inches.

12. The therapeutic healing brassiere of claim 9, wherein each said first pocket and said second pocket cover a majority area of the respective breast in the range of from about 50% to about 80%.

13. The therapeutic healing brassiere of claim 12, wherein said first pad and said second pad include a circular shape with a diameter in the range from about 1 inch to about 8 inches.

\* \* \* \* \*